United States Patent

Blanco

Patent Number: 5,207,664
Date of Patent: May 4, 1993

[54] DISPOSABLE DIAPER CONSTRUCTION

[76] Inventor: Deborah M. Blanco, 11400 NE. 132nd St. Apt. J106, Kirkland, Wash. 98034

[21] Appl. No.: 714,506

[22] Filed: Jun. 13, 1991

[51] Int. Cl.$^5$ .................. A61F 13/15; A61F 13/20
[52] U.S. Cl. ............... 604/385.2; 604/385.1; 604/358
[58] Field of Search ............ 604/385.1, 385.2, 358

[56] References Cited

U.S. PATENT DOCUMENTS

| | | | |
|---|---|---|---|
| 4,640,859 | 2/1987 | Hansen et al. | 604/385.2 X |
| 4,657,539 | 4/1987 | Hasse | 604/385.2 |
| 4,662,877 | 5/1987 | Williams | 604/385.2 |
| 4,663,106 | 5/1987 | Pomplun et al. | 98/40.27 X |
| 4,695,278 | 9/1987 | Lawson | 604/385.2 |
| 4,775,375 | 10/1988 | Aledo | 604/385.2 X |
| 4,790,836 | 12/1988 | Brecher | 604/359 |
| 4,808,177 | 2/1989 | DesMarais et al. | 604/385.2 X |
| 4,816,026 | 3/1989 | Richardson | 604/385.2 |
| 4,842,596 | 6/1989 | Kielpikowski et al. | 604/385.2 |
| 4,909,803 | 3/1990 | Aziz et al. | 604/385.2 |
| 4,917,682 | 4/1990 | Lancaster et al. | 604/385.2 |

Primary Examiner—Randall L. Green
Assistant Examiner—Elizabeth M. Burke
Attorney, Agent, or Firm—Leon Gilden

[57] ABSTRACT

A disposable diaper formed of biodegradable materials includes an outer fabric sheet coextensively and adherably mounted to a fibrous underlying sheet, with a fluid absorbing fabric matrix mounted medially of the fibrous sheet and an inner porous sheet mounted coextensively to the fabric matrix web utilizing heat activated adhesive for securement of the layers together. Side edge recesses are formed medially of each side of the outer fabric sheet and the fibrous sheet, with an elastomeric heat shrinkable thread directed through the outer fabric sheet and fibrous sheet between the recess and the inner porous sheet and the heat activated adhesive.

1 Claim, 4 Drawing Sheets

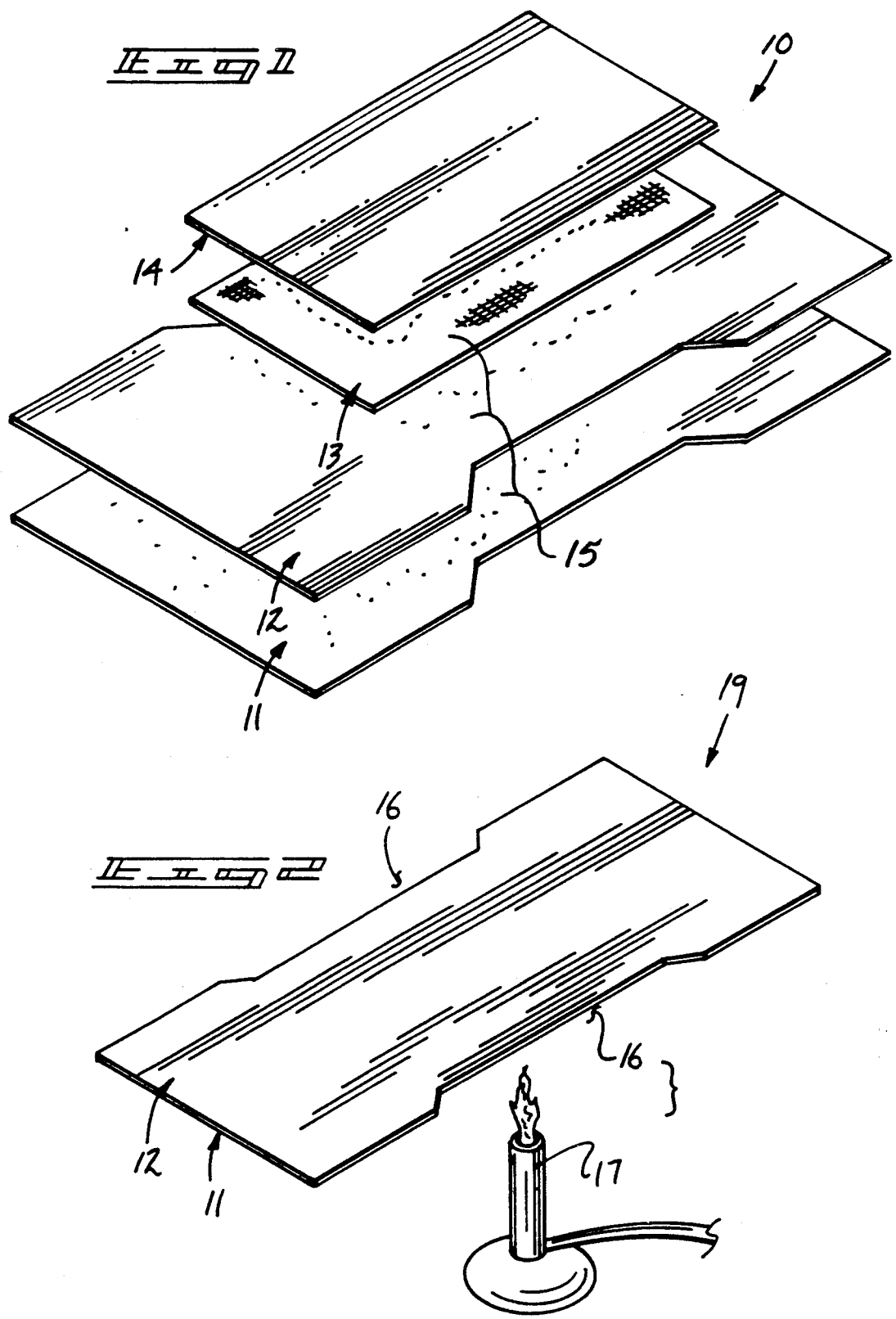

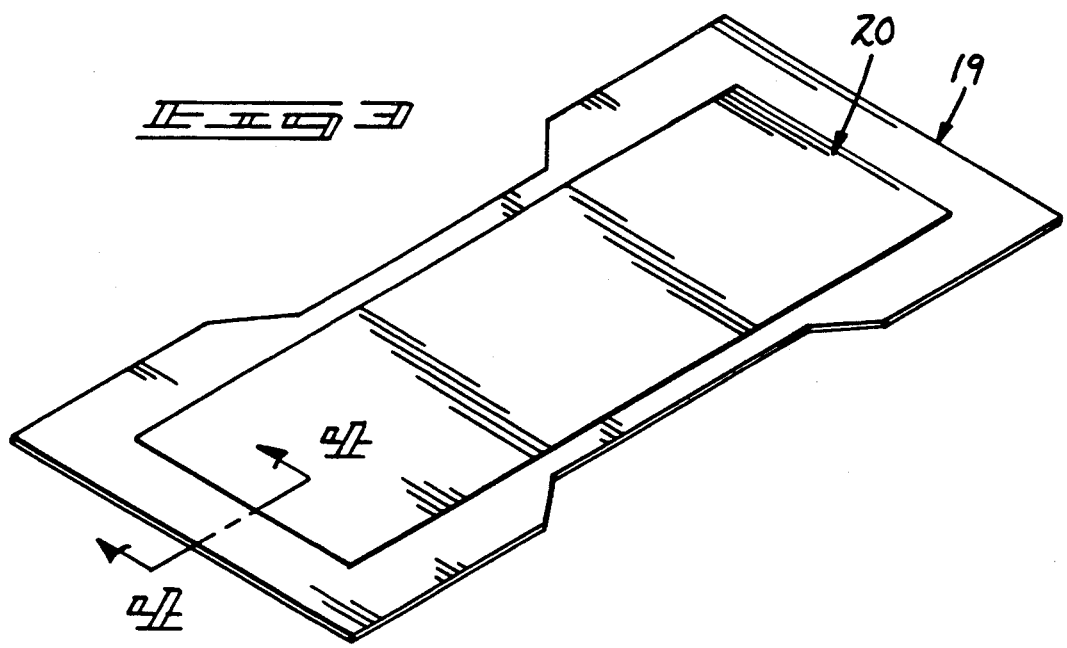
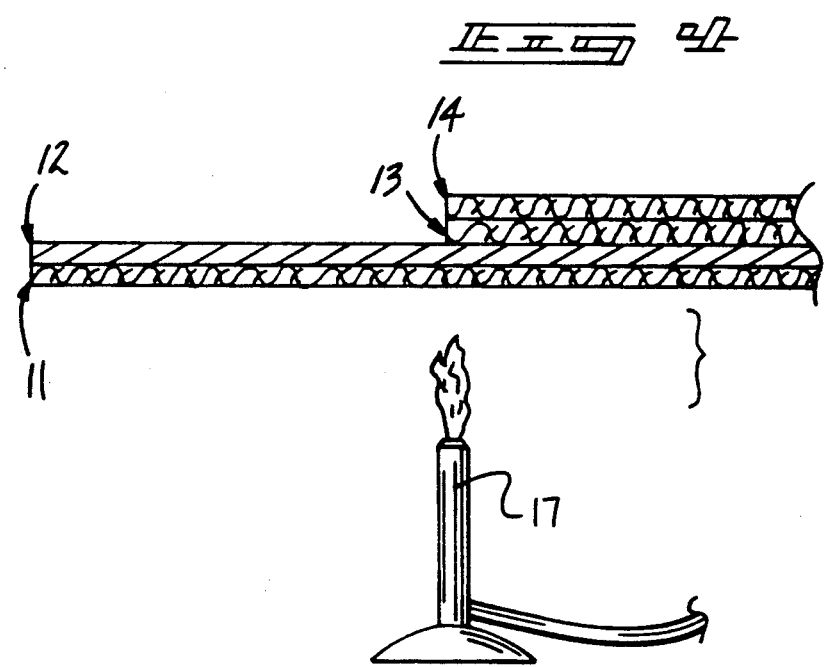

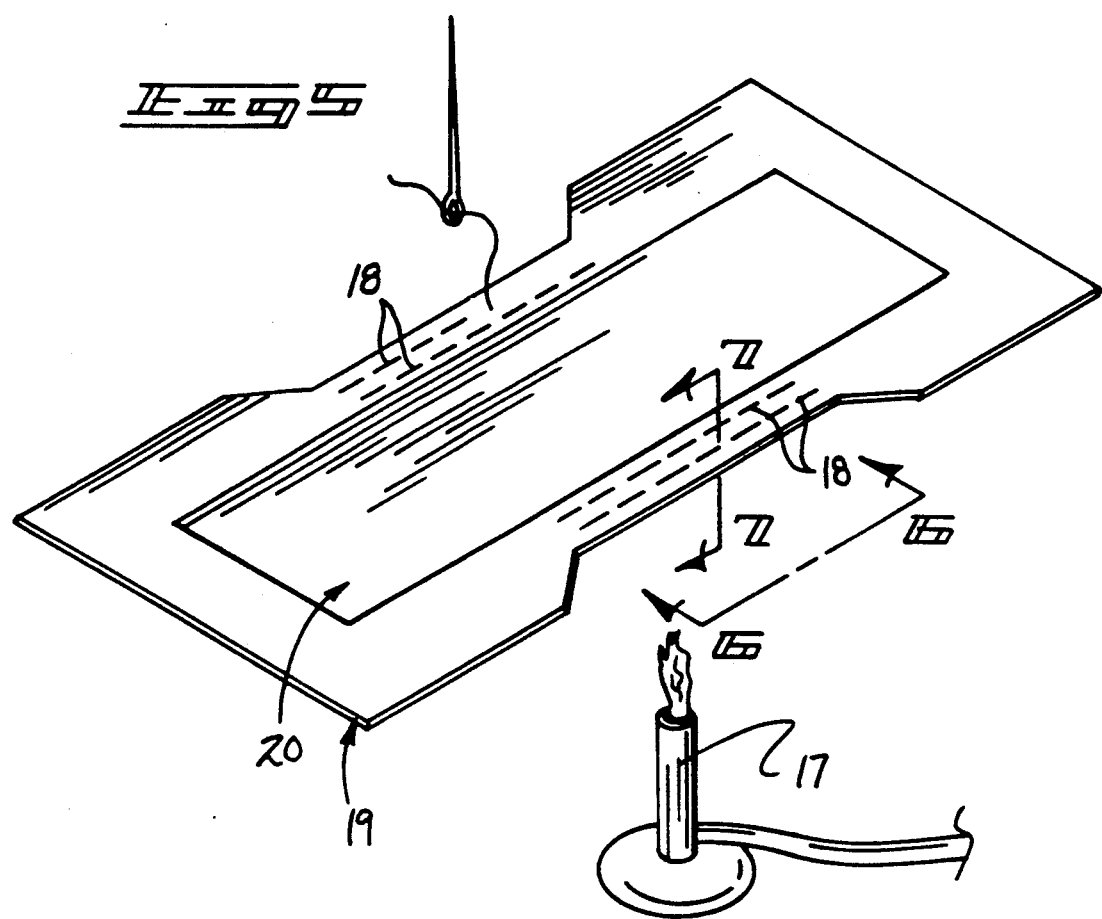
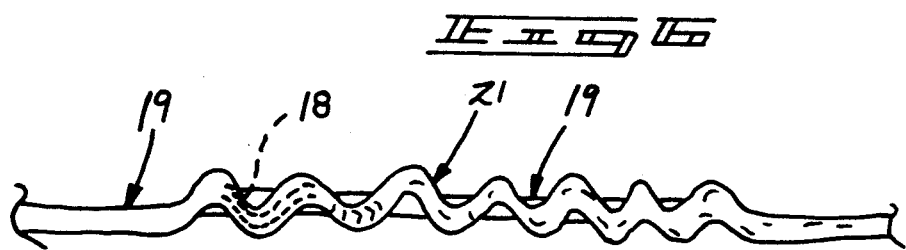

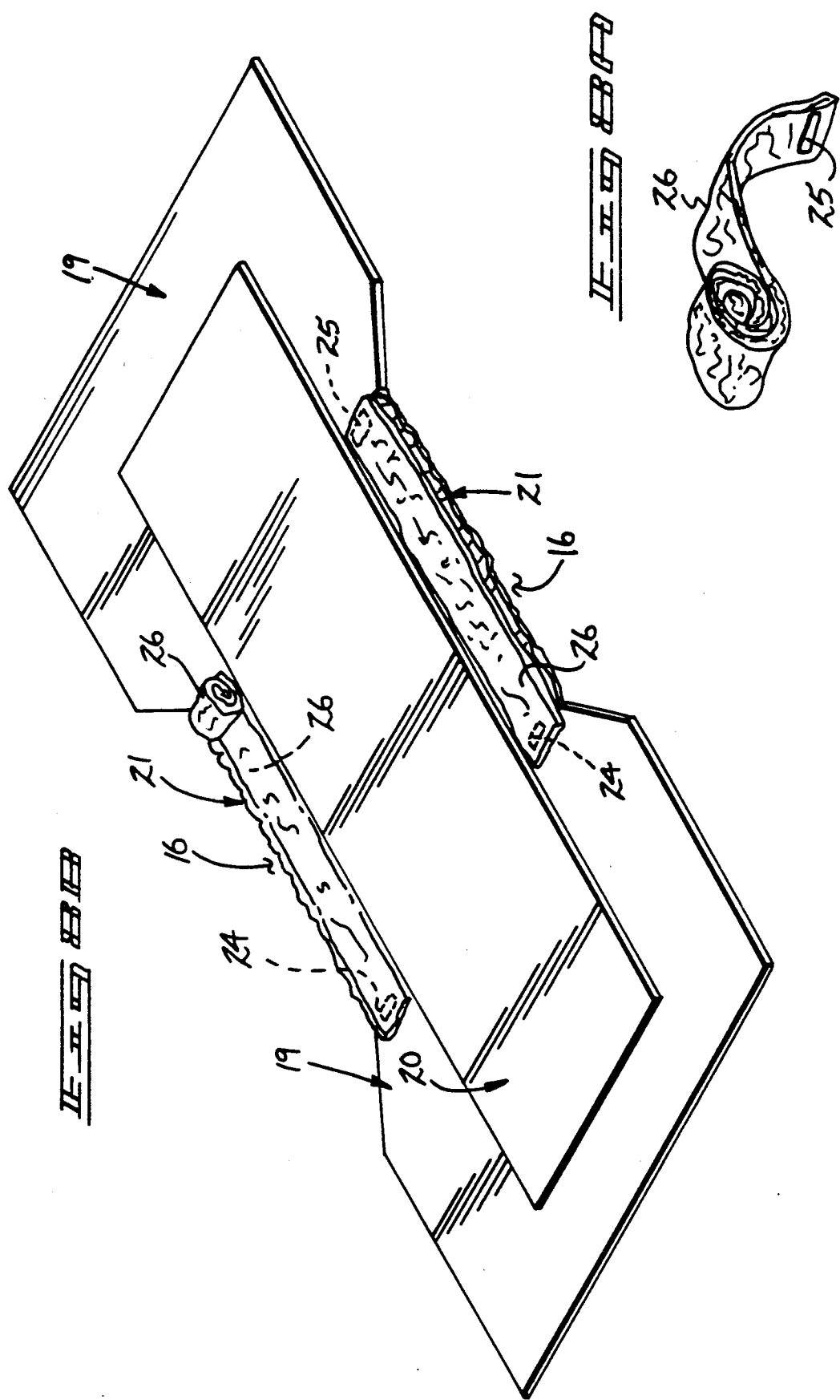

5,207,664

DISPOSABLE DIAPER CONSTRUCTION

BACKGROUND OF THE INVENTION

1. Field of the Invention

The field of invention relates to diaper construction, and more particularly pertains to a new and improved disposable diaper construction wherein the same is formed of biodegradable materials permitting reuse or safe disposal thereof.

2. Description of the Prior Art

Contemporary use of polymeric type diaper construction has provided associated disposal problems with many land fills contemplating restriction of such material. The instant invention attempts to provide a convenient and readily formed diaper construction wherein the same permits ease of disposal thereof.

Examples of the prior art include U.S. Pat. No. 4,816,026 to Richardson providing for a diaper construction of contemporary design utilizing various layering techniques.

U.S. Pat. No. 4,790,836 to Brecher sets forth a plurality of layers mounted within a diaper construction utilizing a polymeric fluid impermeable outer layer.

U.S. Pat. No. 4,897,084 to Ternstrom, et al. sets forth a diaper construction wherein perimeter sides are utilized.

U.S. Pat. No. 4,892,528 to Suzuki sets forth a disposable diaper utilizing a water impervious back sheet.

U.S. Pat. No. 4,834,737 to Kahn sets forth a diaper with a removable absorbent pad mounted medially and longitudinally of the diaper.

As such, it may be appreciated that there continues to be a need for a new and improved disposable diaper construction as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of diaper constructions now present in the prior art, the present invention provides a disposable diaper construction wherein the same utilizes a plurality of laminated sheets formed of biodegradable material. As such, the general purpose of the present invention, which will be described subsequently in greater detail, is to provide a new and improved disposable diaper construction which has all the advantages of the prior art disposable diaper constructions and none of the disadvantages.

To attain this, the present invention provides a disposable diaper formed of biodegradable materials including an outer fabric sheet coextensively and adherably mounted to a fibrous underlying sheet, with a fluid absorbing fabric matrix mounted medially of the fibrous sheet and an inner porous sheet mounted coextensively to the fabric matrix web utilizing heat activated adhesive for securement of the layers together. Side edge recesses are formed medially of each side of the outer fabric sheet and the fibrous sheet, with an elastomeric heat shrinkable thread directed through the outer fabric sheet and fibrous sheet between the recess and the inner porous sheet and the heat activated adhesive.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved disposable diaper construction which has all the advantages of the prior art disposable diaper constructions and none of the disadvantages.

It is another object of the present invention to provide a new and improved disposable diaper construction which may be easily and efficiently manufactured and marketed.

It is a further object of the present invention to provide a new and improved disposable diaper construction which is of a durable and reliable construction.

An even further object of the present invention is to provide a new and improved disposable diaper construction which is susceptible of a low cost of manufacture with regard to both materials and labor, and which accordingly is then susceptible of low prices of sale to the consuming public, thereby making such disposable diaper construction economically available to the buying public.

Still yet another object of the present invention is to provide a new and improved disposable diaper construction which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the plurality of layers utilized by the diaper construction of the instant invention.

FIG. 2 is an isometric illustration of the plurality of outer layers secured together to form a composite outer sheet.

FIG. 3 is an isometric illustration of the composite outer sheet formed to the inner plurality of layers defined as an inner sheet.

FIG. 4 is an orthographic view, taken along the lines 4—4 of FIG. 3 in the direction indicated by the arrows.

FIG. 5 is an isometric illustration of the heat shrinkable elastomeric seam depicted within the sides of the inner sheets.

FIG. 6 is an orthographic view, taken along the lines 6—6 of FIG. 5 in the direction indicated by the arrows.

FIG. 7 is an orthographic view, taken along the lines 7—7 of FIG. 5 in the direction indicated by the arrows.

FIG. 8a is an isometric illustration of a protective pad utilized by the instant invention adherably mounted to the composite outer sheet.

FIG. 8b is an isometric illustration of the protective pad structure mounted to the composite outer sheet and composite inner sheet construction of the instant invention.

DESCRIPTION OF THE PREFERRED EMBODIMENT

With reference now to the drawings, and in particular to FIGS. 1 to 8b thereof, a new and improved disposable diaper construction embodying the principles and concepts of the present invention and generally designated by the reference numeral 10 will be described.

More specifically, the disposable diaper construction 10 of the instant invention essentially comprises an outer fabric sheet 11 formed of a natural fiber, such as cotton, coextensively adhered to a bottom surface of a fibrous sheet 12 utilizing a paper-type web for example. A fluid absorbing fabric matrix web utilizing cotton batting for example is depicted as the member 13 and defined by a predetermined configuration to be positioned completely within the fibrous sheet 12 and adhered thereto by heat activated adhesive 15 utilizing a heat source 17 for such securement. The fluid absorbing fabric matrix web 13 is defined by a predetermined length and width less than a further predetermined length and width defined by the fibrous sheet 12. An inner porous sheet 14 formed of a fibrous material utilizing cotton and a paper matrix is coextensively mounted to a top surface of the fluid absorbing fabric matrix web 13. The sheets 11 and 12 are adhered together utilizing the heated activated adhesive 15 by heat source 17 to define a composite outer sheet 19. The fabric matrix web 13 and the inner porous sheet 14 are secured together to form a composite inner sheet 20. Side edge recesses 16 are formed medially within the opposed elongate sides of the composite outer sheet 19, with the composite inner sheet 20 positioned between the side edge recesses 16 defining a spacing. A heat shrinkable elastomeric thread (see FIG. 5 for example) is directed within the spacing between the composite inner sheet 20 and the side edge recesses 16 to provide a ruffled side wall portion 21 along each of the side edge recesses adjacent side edges of the composite inner sheet 20 to enhance securement of the diaper construction relative to an infant.

A modification of the invention includes a plurality of fibrous protective pads 26 that each include a respective first and second adhesive panel 24 and 25 formed to opposed terminal ends thereof for securement to the top surface of the composite outer sheet 19 to overlie the ruffled side wall portions 21 and defined by a predetermined thickness substantially equal to the predetermined thickness of the composite inner sheet 20 to afford comfort in the use of the garment by an infant to minimize abrasion of the ruffled portions 21 relative to an infant's delicate skin.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A disposable diaper construction, comprising,
   an outer fabric sheet, with a fibrous sheet member coextensively mounted to the outer fabric sheet utilizing a heat activated adhesive therebetween to define a composite outer sheet, and
   the composite outer sheet defined by a predetermined length and a predetermined width, and including spaced side edges, and
   the spaced side edges each include a side edge recess directed medially within the composite outer sheet along each side edge, and
   a fluid absorbing fabric matrix web defined by a further predetermined length and a further predetermined width less than the predetermined length and predetermined width of the composite outer sheet is adhesively mounted medially on a top surface of the composite outer sheet between the side edge recesses, and
   the fabric matrix web is adhesively secured to an inner porous sheet, wherein the fabric matrix web and the inner porous sheet are coextensive relative to one another and define a composite inner sheet, the composite inner sheet defines a predetermined spacing between the composite inner sheet and the side edge recesses of the composite outer sheet, and
   the composite outer sheet includes a plurality of heat shrinkable elastomeric threads directed through the composite outer sheet between the side edge recesses and the composite inner sheet to define ruffled side wall portions between the side edge recesses and the composite inner sheet, and a plurality of protective pads, each protective pad formed of a fibrous material and includes a first and second terminal end and a bottom surface, and each bottom surface including a respective first and second adhesive member mounted adjacent each respective first and second terminal end of each protective pad, and each protective pad is defined by a pad length substantially equal to a recess length defined by each side edge recess, each said protective pad is adherably mounted to the top surface of the composite outer sheet between each side recess and the composite inner sheet to overlie the ruffled side wall portion adjacent each side edge recess, with the first and second adhesive members of each protective pad mounted to the top surface of the composite outer sheet.

* * * * *